United States Patent [19]

Nambu et al.

[11] Patent Number: 5,596,056
[45] Date of Patent: Jan. 21, 1997

[54] PROCESS FOR PRODUCING POLYMER PARTICLES WITH IRREGULAR SHAPE BY POLYMERIZING A WATER-SOLUBLE POLYMERIZABLE MONOMER

[75] Inventors: Hiromi Nambu; Takahide Minami; Takayuki Amiya; Akihiro Kondo, all of Wakayama, Japan

[73] Assignee: Kao Corporation, Tokyo, Japan

[21] Appl. No.: 132,971

[22] Filed: Oct. 7, 1993

[30] Foreign Application Priority Data

Oct. 23, 1992 [JP] Japan .................. 4-286439
Jun. 14, 1993 [JP] Japan .................. 5-142281

[51] Int. Cl.$^6$ ........................... C08F 2/32
[52] U.S. Cl. ............... 526/207; 526/200; 526/211; 526/209
[58] Field of Search ................ 526/207, 200, 526/210, 209

[56] References Cited

U.S. PATENT DOCUMENTS 4,683,274  7/1987  Nakamura .................. 526/216
5,149,750  9/1992  Niessner ..................... 526/81
5,210,159  5/1993  Aoyama ...................... 526/81

FOREIGN PATENT DOCUMENTS 0176664   4/1986  European Pat. Off. .
0182282   5/1986  European Pat. Off. .
57-167302 10/1982  Japan .
61-200102  9/1986  Japan .
62-106902  5/1987  Japan .

*Primary Examiner*—Christopher Henderson
*Attorney, Agent, or Firm*—Birch, Stewart, Kolasch & Birch, LLP

[57]  ABSTRACT

The process of the present invention for producing polymer particles with an irregular shape by polymerizing a water-soluble polymerizable monomer in a system comprising a hydrophobic organic solvent inert to the polymerization and an aqueous solution of the water-soluble polymerizable monomer is characterized in that the system a glycoside compound having such a structure that the hydrogen atom of the hemiacetal bond in the compound has been substituted for a hydrophobic group, or a gluconamide compound as a dispersant.

5 Claims, 1 Drawing Sheet

PROCESS FOR PRODUCING POLYMER PARTICLES WITH IRREGULAR SHAPE BY POLYMERIZING A WATER-SOLUBLE POLYMERIZABLE MONOMER

BACKGROUND OF THE INVENTION

1. Field of the Invention

The present invention relates to a process for producing polymer particles with an irregular shape useful as a water-absorbent resin having a small apparent specific gravity and being excellent in water absorption, gas permeability and liquid permeability and also in gel strength after water absorption.

2. Description of the Prior Art

Water-absorbent resins have found a wide variety of applications in the fields of medical service, such as sanitary materials, food industry and agricultural technology, etc., by taking advantage of their capabilities of water absorption and water retention. In particular, when the absorbent resins are used in sanitary materials, such as sanitary articles, disposable diapers, etc., a large water absorption per unit weight and a high absorption rate are required of them. The water absorption depends upon the molecular structure of the resin, and it is considered that, among the resins having the same weight, the smaller the particle diameter of the resin powder, the larger the specific surface area and the higher the water absorption rate. For this reason, various proposals have been made for processes for producing a water-absorbent resin comprising a resin powder having a small particle diameter and being suitable for a water-absorbent resin.

For example, Japanese Patent Laid-Open No. 167302/1982 proposes an attempt to improve the water absorption rate by conducting polymerization using a particular surfactant as a dispersion stabilizer for polymerization to provide a water-absorbent resin powder having a particle size reduced to 1 to 40 μm. However, mere pulverization of the water-absorbent resin causes the formation of curd during water absorption, so that no sufficient water absorption rate can be attained.

Japanese Patent Laid-Open No. 106902/1987 describes a process for producing a water-absorbent porous polymer having pores in the inside thereof and a high specific surface area, which comprises preparing an O/W/O emulsion of a monomer and polymerizing the monomer. In this process, however, the step of preparing the O/W/O emulsion is troublesome, and the pores of the resultant polymer are not always interconnected with each other, so that no water-absorbent resin having a satisfactory initial water absorption rate can be produced.

On the other hand, Japanese Patent Laid-Open No. 200102/1986 proposes a process for producing water-absorbent resin particles, which comprises initiating W/O type reverse phase suspension polymerization at 0° to 20° C., holding the reaction system at that temperature until the degree of polymerization reaches 30%, and raising the temperature to complete the polymerization. It discloses that this process provides water-absorbent resin particles wherein fine particles having a size of 1 to 40 μm are relatively loosely bonded to each other and the particles have a high void fraction, are porous, and have a high water absorption rate. In this process, it is necessary above all to control the polymerization temperature to be in the range of 0° to 20° C. until the conversion reaches 30%. It is very difficult, however, to control the polymerization temperature by efficiently removing the heat of polymerization at such a low temperature, which renders this process unsuitable for the mass production of water-absorbent resin particles. Further, the process is disadvantageous in that it is poor in productivity because a large amount of the polymer deposits on a polymerization vessel in the course of the reaction.

SUMMARY OF THE INVENTION

Accordingly, an object of the present invention is to provide a process for producing polymer particles with an irregular shape useful as a water-absorbent resin having a small apparent specific gravity and being excellent in water absorption capacity such as initial water absorption rate, gas permeability and liquid permeability and also in gel strength after water absorption, which process is simple in operation and excellent in productivity, and enables the polymer particles to be mass produced.

The present inventors have made intensive studies and, as a result, have found that the above-described object can be attained by using a specified glycoside or gluconamide compound as a dispersant in the polymerization of a water-soluble polymerizable monomer.

The present invention, which has been made on the basis of the above-described finding, provides a process for producing polymer particles with an irregular shape by polymerizing a water-soluble polymerizable monomer in a system comprising a hydrophobic organic solvent inert to the polymerization and an aqueous solution of the water-soluble polymerizable monomer, which process is characterized in that the system further contains a glycoside compound having such a structure that the hydrogen atom of a hemiacetal bond in the compound has been substituted for a hydrophobic group or a gluconamide compound as a dispersant.

The polymer particles with an irregular shape produced by the process of the present invention have a shape utterly different from a spherical one (a non-spherical shape) and an average particle diameter of 10 μm or larger as measured by the sieving method (JIS) and a high void fraction, thus imparting a high water absorption rate and excellent gas permeability, liquid permeability and gel strength after water absorption to a water-absorbent resin as an aggregate of such polymer particles.

According to the present invention, it s possible to produce polymer particles with an irregular shape useful as a water-absorbent resin having a low apparent specific gravity and being excellent in water absorption capacity such as initial water absorption rate, gas permeability and liquid permeability and also in gel strength after water absorption through a simple operation at an excellent productivity in a mass-producible manner by polymerizing a water-soluble polymerizable monomer in the presence of a specified dispersant.

Therefore, the polymer particles having an irregular shape produced by the process of the present invention are useful as a water-absorbent polymer to be used in sanitary materials which come in contact with the human body, for example, sanitary napkins, paper diapers, sheets for adults, tampons and sanitary cottons by virtue of the particularly excellent water absorption. Further, since the polymer of the present invention is less susceptible to deterioration in gel structure even when used for a long period of time, and further is highly elastic, it can be used as a water-retaining agent for various horticultural purposes and a water cutoff agent for civil engineering works and construction and further can be expected to be applied to cosmetics wherein importance is attached to the shape, elasticity, water absorption and gas permeability.

DETAILED DESCRIPTION OF THE INVENTION

Figure 1:
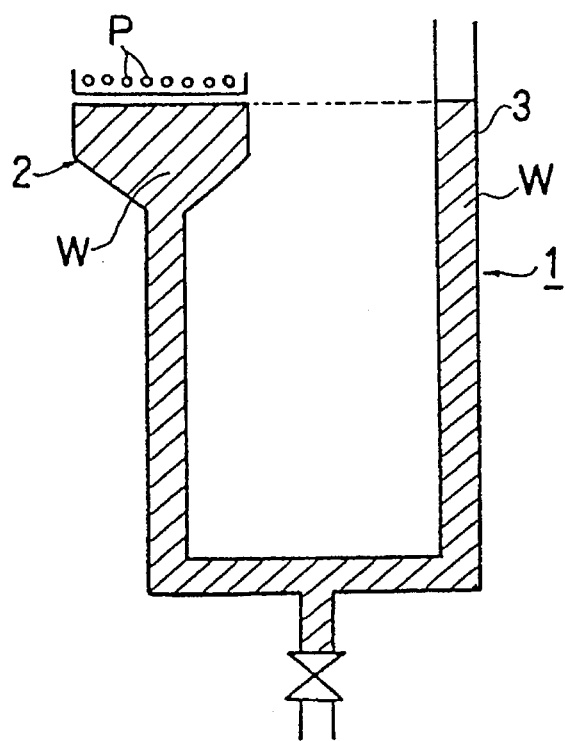
FIG. 1 is a schematic view of an apparatus for measuring the water absorption as a measure of the water absorption rate which is used in the Examples and Comparative Examples.

The process for producing polymer particles with an irregular shape according to the present invention will now be described. In the description, "%" is "% by weight" unless otherwise specified.

Preferable examples of the water-soluble polymerizable monomer to be used in the present invention include vinyl monomers having a polymerizable unsaturated group, such as olefinically unsaturated carboxylic acids and salts thereof, olefinically unsaturated carboxylic acid esters, olefinically unsaturated sulfonic acids and salts thereof, olefinically unsaturated phosphoric acids and salts thereof, olefinically unsaturated amines, olefinically unsaturated ammonium salts and olefinically unsaturated amides. Among them, olefinically unsaturated carboxylic acids or salts thereof are particularly preferred in the present invention.

Examples of the olefinically unsaturated carboxylic acids and salts thereof include acrylic, methacrylic, maleic and fumaric acids and alkali salts thereof. Examples of the olefinically unsaturated carboxylic acid esters include methoxypolyethylene glycol(meth)acrylate, phenoxypolyethylene glycol(meth)acrylate and hydroxyethyl(meth)acrylate. Examples of the olefinically unsaturated sulfonic acids and salts thereof include (meth)acrylamidomethylpropanesulfonic and allylsulfonic acids and alkali salts thereof. Examples of the olefinically unsaturated phosphoric acids and salts thereof include (meth)acryloyl(poly)oxyethylenephosphoric esters and alkali salts thereof. Examples of the olefinically unsaturated amines include dimethylaminoethyl(meth)acrylate. Examples of the olefinically unsaturated ammonium salts include (meth)acryloyloxyethylenetrimethylammonium halides. Examples of the olefinically unsaturated amides include (meth)acrylamide and (meth)acrylamide derivatives such as N-methyl(meth)acrylamide, N-ethyl(meth)arylamide and N-propyl(meth)acrylamide, and vinylmethylacetamide. They may be used either alone or in the form of a mixture of two or more of them. Examples of the alkali salts include alkali metal salts, alkaline earth metal salts and ammonium salts.

The concentration of the water-soluble polymerizable monomer in an aqueous solution thereof is preferably 1 to 90%, still preferably 10 to 60%.

In the present invention, examples of the hydrophobic organic solvent inert to the polymerization include aliphatic hydrocarbons such as n-pentane, cyclopentane, n-hexane, cyclohexane, n-heptane and methylcyclohexane, aromatic hydrocarbons such as benzene and toluene, aliphatic alcohols having 4 to 6 carbon atoms, such as n-butyl alcohol and n-amyl alcohol, aliphatic ketones such as methyl ethyl ketone, and aliphatic esters such as ethyl acetate. They may be used alone or in the form of a mixture of two or more of them.

The amount of the hydrophobic organic solvent used preferably ranges from 50 to 500% based on the aqueous solution of the water-soluble polymerizable monomer.

The dispersant to be used in the polymerization of the above-described water-soluble polymerizable monomer in the present invention is a glycoside compound having a structure wherein the hydrogen atom of the hemiacetal bond has been replaced with a hydrophobic group (hereinafter referred to as "glycoside compound A") or a gluconamide compound.

The glycoside compounds A are those derived from the following saccharides by replacing the hydrogen atom of the hemiacetal bond thereof with a hydrophobic group: pentoses such as ribose, arabinose, xylose, lyxose and ribulose; monosaccharides such as allose, altrose, glucose, mannose, gulose, idose, galactose, talose and fructose as well as condensates of them; maltooligosaccharides such as maltose, isomaltose, isomaltotriose and cyclodextrin; cellooligosaccharides such as cellobiose; and oligosaccharides such as galactooligosaccharide, mannooligosaccharide, fructooligosaccharide, sucrose and lactose.

The hydrophobic groups include alkyl and alkenyl groups having at least 6 carbon atoms, preferably at most 22 carbon atoms, alkylaryl groups, polyoxyalkylenealkyl groups and alkylphenyl groups; and acyloxyhydroxypropyl and alkoxyhydroxypropyl groups in which the acyloxy or alkoxy group has at least 6 carbon atoms, preferably at most 22 carbon atoms. Examples include octyl, decyl, dodecyl octadecyl, octadecenyl and 3-octadecanoyl-2-hydroxypropyl groups.

The glycoside compounds A are not particularly limited and compounds represented by the following formula 1 are preferred:

Formula 1

wherein $R^1$ represents a linear or branched alkyl, alkenyl group, or an alkylphenyl group having 6 to 22 carbon atoms, or a hydroxyacyloxyalkyl group having at least 9 carbon atoms, $R^2$ represents an alkylene group having 2 to 4 carbon atoms, G represents a reducing sugar residue having 5 or 6 carbon atoms, x represents a number of 0 to 10 on average and y represents a number of 1 to 10 on average, with the proviso that when x is 2 or above, then $R^2$ may be the same or different from each other, and the hydrogen atom of the hydroxyl group in G may be substituted by a methyl or ethyl group or a unit having 12 or fewer carbon atoms and at least one hydrophilic group such as an ether oxygen, ester group, amido group, ionic group, hydroxyl group or ammonium group.

In the above formula 1, $R^1$ is preferably an alkyl, alkenyl or an alkylphenyl group having 6 to 22 carbon atoms, or a hydroxy-acyloxypropyl group having 9 to 25 carbon atoms and x is preferably 0.

The compounds of the above formula 1 are preferably compounds of the following formula 2, and alkyl glucosides and alkyl polyglucosides of the above formula 1 wherein the hydrogen atom of the hydroxyl group in G is replaced with a functional group of the following formulae 3 through 9, and derivatives of them. In the compounds of the above formula 2, those wherein $R^3$ has 8 to 18 carbon atoms are preferred.

Examples of them include dodecyl glucoside, decyl glucoside, tetradecyl glucoside, 6-polyoxypropylenedodecyl glucoside, octyl glucoside, 3-octadecanoyloxy-2-hydroxypropyl glucoside, dodecyl galactoside and dodecyl fructoside.

Formula 2

$$R^3 G'_{y'}$$

wherein $R^3$ represents a linear or branched alkyl, alkenyl group, or an alkylphenyl group having 6 to 22 carbon atoms, or a hydroxyacyloxyalkyl group having 9 to 25 carbon atoms, G' represents a reducing sugar residue having 5 or 6 carbon atoms and y' represents a number of 1 to 6 on average.

Formula 3

$$-(CH_2CHO)_{\overline{m1}}-H$$
$$\quad\quad\;\;|$$
$$\quad\quad CH_3$$

wherein m1 represents a number of 0 to 10.

Formula 4

$$-(CH_2CH_2O)_{\overline{m2}}-H$$

wherein m2 represents a number of 0 to 10,

Formula 5

$$-(CH_2)_{\overline{m3}}-CO_2Na,$$

wherein m3 represents a number of 0 to 10,

Formula 6

$$-(CH_2CH_2O)_{\overline{m4}}-SO_3Na$$

wherein m4 represents a number of 0 to 10,

Formula 7

$$-CH_2CHCH_2OH,$$
$$\quad\;\;|$$
$$\quad OH$$

Formula 8

$$\quad O$$
$$\quad \|$$
$$-C-CH_2CHCO_2Na$$
$$\quad\quad\quad\;\;|$$
$$\quad\quad\quad SO_3Na$$

Formula 9

$$-P(OH)_2$$
$$\;\;\|$$
$$\;\;O$$

As the compounds of the above formula 1, those of the following formula 10 are preferred.

Formula 10

$$R^4 G''_{y''}$$

wherein $R^4$ represents a linear or branched alkyl, alkenyl group, or alkylphenyl group having 6 to 22 carbon atoms, or a hydroxyacyloxyalkyl group having 9 to 25 carbon atoms, G" represents a reducing sugar residue having 5 or 6 carbon atoms wherein the hydrogen atom of the hydroxyl group is substituted for a polyoxyethylene, polyoxypropylene or polyglyceryl group and y" represents a number of 1 to 6 on average.

In the compounds of the above formula 10, preferred are those wherein $R^4$ has 8 to 18 carbon atoms and the degree of polymerization of the hydroxyethylene, hydroxypropylene or glycerol group is 0 to 4.

The gluconamide compounds include those produced by reacting one of the following amines with gluconolactone: n-butylamine, sec-butylamine, t-butylamine, n-pentylamine, n-hexylamine, n-heptylamine, 2-ethylhexylamine, n-octylamine, n-nonylamine, n-decylamine, n-undecylamine, n-dodecylamine, n-tridecylamine, n-tetradecylamine, n-hexadecylamine, n-octadecylamine, n-eicosylamine, diisobutylamine, di-n-butylamine, di-2-ethylexylamine, 3-methoxypropylamine, 3-ethoxypropylamine, benzylamine, toluidine, naphthylamine and p-ethoxyaniline.

Although the gluconamide compounds are not particularly limited, preferred are compounds of the following formula 11, still preferred are compounds of the following formula 12 and particularly preferred are compounds of the following formula 13:

Formula 11

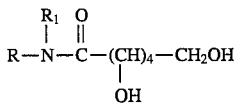

wherein R and $R_1$ each represents a hydrogen atom, a linear or branched alkyl or alkenyl group having 5 to 25 carbon atoms, a phenyl group or an alkylaryl group having 7 to 25 carbon atoms, with the proviso that not both of R and $R_1$ are hydrogen atoms at the same time, and R and $R_1$ may contain a functional group such as a hydroxyl, ether, oxyalkylene or acetyl group.

Formula 12

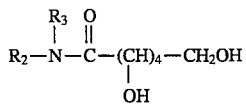

wherein $R_2$ and $R_3$ each represents a hydrogen atom, a linear or branched alkyl or alkenyl group having 5 to 25 carbon atoms, a phenyl group or an alkylaryl group having 7 to 25 carbon atoms, with the proviso that not both of $R_2$ and $R_3$ are hydrogen atoms at the same time.

Formula 13

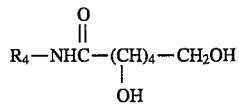

wherein $R_4$ represents a linear or branched alkyl or alkenyl group having 5 to 25 carbon atoms, a
phenyl group or an alkylaryl group having 7 to 25 carbon atoms.

Particularly preferred gluconamide compounds are those of the above formula 11, general formula 12 and formula 13 wherein R represents an alkyl, alkenyl or alkylphenyl group having 8 to 18 carbon atoms. Examples of them include N-(n-decyl)gluconamide, N-(n-dodecyl)-gluconamide, N-(n-tetradecyl)gluconamide, N-(n-hexadecyl)gluconamide and N-(n-octadecyl)gluconamide.

Although a satisfactory effect can be attained even when the glycoside compound A or gluconamide compound is used alone as a dispersant, they can be used in the form of a mixture of two or more of them.

The effect of the dispersant can be attained even when the amount thereof is small, and this amount preferably ranges from 0.01 to 20%, still preferably from 0.02 to 10%, still more preferably from 0.05 to 10% based on the water-soluble polymerizable monomer.

The water-soluble polymerizable monomer can be polymerized in a system comprising a hydrophobic organic solvent inert to the polymerization and an aqueous solution of the water-soluble polymerizable monomer, for example, by the following processes (1) to (4):

(1) a process comprising mixing an aqueous solution of a water-soluble polymerizable monomer with a hydrophobic organic solvent at once and then polymerizing the monomer (batch polymerization);
(2) a process comprising conducting polymerization successively while dropwise adding an aqueous solution of a water-soluble polymerizable monomer to a hydrophobic organic solvent (successive polymerization);
(3) a process comprising conducting polymerization while dropwise adding a mixed solution produced by previously mixing or dispersing an aqueous solution of a water-soluble polymerizable monomer in part of a hydrophobic organic solvent to a hydrophobic organic solvent (predispersion); and
(4) a process wherein the processes (1) to (3) are used in combination.

In conducting the polymerization, the dispersant is incorporated in the reaction system by, for example, the following methods (1) to (4):

(1) a method wherein the glycoside compound A or the gluconamide compound is previously dispersed in a hydrophobic organic solvent;
(2) a method wherein the glycoside compound A or the gluconamide compound is previously dissolved or dispersed in an aqueous solution of a water-soluble polymerizable monomer;
(3) a method wherein the glycoside compound A or the gluconamide compound is gradually added while conducting the polymerization; and
(4) a method wherein the methods (1) to (3) are employed in combination.

In conducting the polymerization, it is preferred to use a polymerization initiator. There is no particular limitation on the polymerization initiator so far as it is a water-soluble free-radical initiator. Examples thereof include ketone peroxides, such as methyl ethyl ketone peroxide and methyl isobutyl ketone peroxide, dialkyl peroxides such as di-tert-butyl peroxide and tert-butyl cumyl peroxide, alkyl peroxy esters, such as tert-butyl peroxyacetate, tert-butyl peroxyisobutyrate and tert-butyl peroxypivalate, hydrogen peroxide, persulfates, such as potassium persulfate and ammonium persulfate, perchlorates, such as potassium perchlorate and sodium perchlorate, halogenic acid salts, such as potassium chlorate and potassium bromate, and azo compounds, such as 2-(carbamoylazo)isobutyronitrile, 2,2-azobis(N,N'-dimethyleneisobutyramidine)dihydrochloride, 2,2'-azobis(2-amidinopropane)dihydrochloride, 2,2'-azobis(N,N'-dimethyleneisobutylamidine), 4,4'-azobis(4-cyanopentanoic acid), azobisisobutyronitrile, 2,2'-azobis(4-methoxy-2,4-dimethylvaleronitrile), (1-phenylethyl)azodiphenylmethane, dimethyl 2,2'-azobisisobutyrate, 2,2'-azobis(2-methylbutyronitrile), 1,1'-azobis(1-cyclohexanecarbonitrile), 2,2'-azobis(2,4,4'-trimethylpentane), 2-phenylazo-2,4-dimethyl-4-methoxyvaleronitrile and 2,2'-azobis(2-methylpropane). They may be used alone or in the form of a mixture of two or more of them.

The amount of the polymerization initiator used usually ranges from 0.01 to 10%, preferably from 0.02 to 5%, based on the water-soluble polymerizable monomer.

Although there is no particular limitation on the method for adding the polymerization initiator, it is preferred to previously add the polymerization initiator to the aqueous solution of the polymerizable water-soluble monomer.

In conducing the polymerization, basically the polymerization temperature is not particularly limited so far as it is within a temperature range in which the water-soluble polymerizable monomer can be polymerized. However, in due consideration of the polymerization temperature and conversion, the polymerization is preferably conducted at a temperature in the optimum polymerization temperature range for the water-soluble polymerizable monomer to be used. The temperature usually ranges from 20° to 150° C., preferably 40° to 100° C.

In the present invention, it is preferred to use only the water-soluble polymerizable monomer as the polymerizable monomer to be homopolymerized or copolymerized. It is also possible, however, to use the water-soluble polymerizable monomer in combination with a water-insoluble monomer copolymerizable therewith, for example, a monomeric ester of an alkanol having 1 to 22 carbon atoms with an unsaturated carboxylic acid such as acrylic, methacrylic, maleic or fumaric acid, which is used in an amount of 50% or less based on the whole monomer.

Besides the above-described hydrophobic solvent, an amphipathic solvent may be added so far as the amount thereof does not exceed that of the hydrophobic solvent. Examples of the amphipathic solvents include alcohols such as methanol, ethanol, propanol and 2 propanol; ketones such as acetone; and ethers such as diethyl ether, dipropyl ether, tetrahydrofuran and dioxane.

Further, besides the dispersant, nonionic surfactants, cationic surfactants, amphoteric surfactants, anionic surfactants, polymeric dispersants, etc., can be used in combination with the above-described dispersant in an amount of preferably 100 parts by weight or less for 100 parts by weight of the dispersant.

In the present invention, a well-known cross-linking agent may be used before, during or after the polymerization. Examples of the crosslinking agents include polyallyl compounds such as N,N-diallyl(meth)acrylamide, diallylamine, diallylmethacrylamine, diallyl phthalate, diallyl maleate, diallyl terephthalate, triallyl cyanurate and triallyl phosphate; polyvinyl compounds such as divinylbenzene, N,N-methylenebisacrylamide, ethylene glycol diacrylate, ethylene glycol dimethacrylate and glycerin trimethacrylate; polyglycidyl ethers such as ethylene glycol diglycidyl ether, polyethylene glycol diglycidyl ether and polyglycerin polyglycidyl ether; haloepoxy compounds such as epichlorohydrin and α-methylchlorohydrin; polyaldehydes such as glutaraldehyde and glyoxal; polyols such as glycerin; polyamines such as ethylenediamine: hydroxy vinyl compounds such as 2-hydroxyethyl methacrylate, and inorgano- and organometallic salts capable of yielding a polyvalent ion, such as those of calcium, magnesium, zinc and aluminum.

Further, it is also possible to use a monoglycidyl compound such as phenol polyoxyethylene glycidyl ether as a modifier.

The amount of the crosslinking agent or modifier may be arbitrary according to desired properties of the polymer as the final product and it is usually preferably in the range of 0.01 to 10% based on the resultant polymer.

The polymer thus produced is dried by means of a vacuum drier, fluid drier or the like, immediately after the polymerization or after the removal of the solvent by decantation or centrifugation to obtain the polymer particles with an irregular shape. The particles thus obtained can be pulverized or granulated, if necessary, to a desired particle diameter.

It is well known that nonionic surfactants such as sorbitan esters and sucrose esters are generally used in the suspension polymerization of a water-soluble monomer to stably produce spherical polymer particles. Although a detailed mechanism of the production of the polymer with an irregular shape has not yet been elucidated, it is conceivable that the above-described glycoside compound A or gluconamide compound suitably and slightly destabilizes the shape of the dispersed particles and also suitably stabilizes the dispersed particles not to aggregate them together, so that a delicate balance between the instability of the shape of the dispersed particles and the resistance of the dispersed particles to aggregation is maintained.

The present invention will now be described in more detail with reference to the following Examples and Comparative Examples, though it is not limited to these Examples only.

In the Examples and Comparative Examples, the following tests were conducted.

[Method for measuring equilibrium swelling water absorption]

1 g of the polymer was dispersed in a large excess of physiological saline (0.9% saline) to swell the polymer until the absorption reaches the equilibrium swelling state. Then, the physiological saline was filtered off through an 80-mesh wire gauze, the weight (W) of the resultant swollen polymer was measured, and this value was divided by the weight ($W_0$) of the polymer before the water absorption to provide a $W/W_0$ value as the equilibrium swelling water absorption (g/g).

[Method for measuring an amount of water absorption as measure of water absorption rate]

A apparatus (Demand Wettability Tester) generally known as a device for practicing the DW test and shown in FIG. 1 was used. As shown in FIG. 1, 0.3 g of polymer P was spread on a polymer spreading stand 2 (a stand wherein No. 2 filter paper having a diameter of 70 mmØ was put on a glass filter No. 1) set in such a manner that the levels of the physiological saline W are equal to each other. The absorption at the time when the polymer was spread was taken as 0 (zero), and the absorption 30 sec after the spreading of the polymer was measured by reading the graduation of a buret indicating the degree of lowering in the level of the physiological saline W. The measured value was taken as the water absorption (ml) as a measure of the water absorption rate.

[Method for measuring passing rate of physiological saline]

Figure 2:
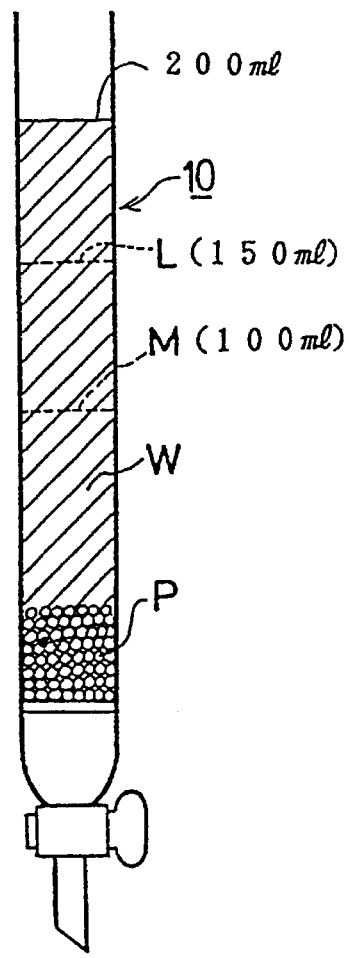
FIG. 2 is a schematic view of an apparatus for measuring the physiological saline passing rate which is used in the Examples and Comparative Examples.

0.5 g of the polymer was packed in an apparatus 10 (a glass cylinderical tube equipped with a cock and having an inner diameter of 25.6 mm and a length of the cylindrical portion of about 500 mm) shown in FIG. 2, and swollen with an excess of physiological saline until the swelling reached equilibrium. The level of the physiological saline was adjusted to a position corresponding to 200 ml from the bottom, and the cock was closed. After the polymer P was sufficiently settled as shown in FIG. 2, the cock was opened to measure the time taken for the physiological saline W to pass through between two marked lines shown in the figure, that is, marked line L (a position corresponding to 150 ml from the bottom) and marked line M (a position corresponding to 100 ml from the bottom) (amount of liquid: 50 ml), and the amount (ml) of liquid between the marked lines was divided by the measurement time (min) to give the passing rate (ml/min).

[Method for calculating average particle diameter]

100 g of the polymer was classified with a JIS sieve and the average particle diameter was determined from the weight proportion of each fraction.

EXAMPLE 1

72.1 g of acrylic acid was diluted with 18.0 of water and neutralized with 98.9 g of a 30 wt. % aqueous sodium hydroxide solution under cooling, 5.6 g of 5.2 wt. % potassium persulfate was added thereto to prepare a homogeneous solution as an aqueous monomer/initiator solution.

Separately, a 500-ml flask equipped with a reflux condenser, a dropping funnel, a stirring rod and a nitrogen gas feed pipe was charged with 283 ml of cyclohexane, and 1.8 g of dodecyl glucoside (degree of saccharide condensation: 1.25) was added thereto. They were stirred (at 300 rpm) and dispersed in each other, and the flask was purged with nitrogen and heated to 75° C. The above-described aqueous monomer/initiator solution was dropwise added thereto over a period of 30 min. After the completion of the addition, the polymerization was conducted under stirring at 75° C. for 1.5 h and then at 80° C. for 4 h. After the completion of the polymerization, the product was fractionated and dried under reduced pressure to provide 88.4 g of a polymer of acrylic acid (sodium salt). The resultant polymer was in the form of granules of a distorted shape having an average diameter of 650 μm and a bulk density of 0.30 g/ml. The surfaces of the polymer particles had such a structure that the particles having irregular shapes and sizes of several to 20 μm were fused each other and the unevenness of the surfaces was very large.

EXAMPLE 2

71.1 g of acrylamide was dissolved in 150 g of water, and 10.7 g of a 2.8 wt. % aqueous 2,2'-azobis(2-amidinopropane)dihydrochloride solution was added thereto to prepare a homogeneous solution as an aqueous monomer/initiator solution. Thereafter, the same procedure as that of Example 1 was repeated, except that n-hexane was used as the solvent instead of cyclohexane, thereby providing 69 g of an acrylamide polymer. The resultant polymer was in the form of granular particles of a distorted shape having an average diameter of 1300 μm and a bulk density of 0.45 g/ml. The surfaces of the polymer particles had such a structure that the particles having irregular shapes and sizes of several to 20 μm ware fused with each other and the unevenness of the surfaces was very large.

EXAMPLE 3

106.6 g of sodium acrylamidomethylpropanesulfonate was dissolved in 150 g of water, and 10.7 g of a 2.8 wt. % aqueous 2,2'-azobis(2-amidinopropane)dihydrochloride solution was added thereto to prepare a homogeneous solution as an aqueous monomer/initiator solution. Thereafter, the same procedure as that of Example 1 was repeated, thereby providing 95 g of sodium acrylamidomethylpropanesulfonate polymer. The resultant polymer was in the form of granular particles of a distorted shape having an average diameter of 1000 μm and a bulk density of 0.52 g/ml. The surfaces of the polymer particles had such a structure that the particles having irregular shapes and sizes of several to 20 μm were fused with each other and the unevenness of the surfaces was very large.

EXAMPLE 4

72.1 g of acrylic acid was diluted with 18.0 g of water and neutralized with 98.9 g of a 30 wt. % aqueous sodium hydroxide solution under cooling, 10.7 g of a 2.8 wt. % aqueous potassium persulfate solution and 0.058 g of an epoxy bifunctional crosslinking agent (ethylene glycol diglycidyl ether) was added thereto to prepare a homogeneous solution as the aqueous monomer/initiator solution. Separately, a 500-ml flask equipped with a reflux condenser, a dropping funnel, a stirring rod and a nitrogen gas feed pipe was charged with 283 ml of cyclohexane, and 1.8 g of dodecyl glucoside (degree of saccharide condensation: 1.25) was added thereto. They were stirred (at 300 rpm) and dispersed in each other, and the flask was purged with nitrogen and heated to 75° C. The above-described aqueous solution of a monomer of acrylic acid (sodium salt) was dropwise added thereto over a period of 30 min. After the completion of the addition, the polymerization was conducted under stirring at 75° C. for 1.5 h and then at 80° C. for 4 h.

After the completion of the polymerization, the product was fractionated and dried under reduced pressure to provide 88.4 g of a polymer of acrylic acid (sodium salt). The resultant polymer was in the form of distorted granular particles having an average diameter of 680 μm and a bulk density of 0.32 g/ml. The surfaces of the polymer particles had such a structure that the particles having irregular shapes and sizes of several to 20 μm were fused with each other and the unevenness of the surfaces was very large.

The equilibrium swelling water absorption, water absorption as a measure of the water absorption rate and physiological saline passing rate of each of the resultant polymers were determined. The results are given in Table 1.

EXAMPLE 5

36.1 g of acrylic acid was dissolved in 16.0 g of water and neutralized with 53.0 g of a 30 wt. % aqueous sodium hydroxide solution under cooling. Thereafter, 101.3 g of a 40 wt. % aqueous sodium acrylamidomethylpropanesulfonate solution was added thereto, and 10.7 g of a 2.8 wt. % aqueous potassium persulfate solution was added thereto to prepare a homogeneous solution as the aqueous monomer/initiator solution. Thereafter, the same procedure as that of Example 4 was repeated, thereby providing 93.5 g of sodium acrylate/sodium acrylamidomethylpropanesulfonate copolymer. The resultant polymer was in the form of distorted granular particles having an average diameter of 550 μm and a bulk density of 0.45 g/ml.

The measurement was conducted on the resultant polymer in the same manner as that of Example 4. The results are given in Table 1.

EXAMPLE 6

The same procedure as that of Example 4 was repeated except that the dodecyl glucoside (degree of saccharide condensation: 1.25) was replaced with tetradecyl glucoside (degree of saccharide condensation: 1.17) as the dispersant, thereby providing distorted granular particles having extremely uneven surfaces. The average particle diameter and bulk density were 850 μm and 0.54 g/ml, respectively.

The measurement was conducted on the resultant polymer in the same manner as that of Example 4. The results are given in Table 1.

EXAMPLE 7

The same procedure as that of Example 4 was repeated except that the dodecyl glucoside (degree of saccharide condensation: 1.25) was replaced with tetradecyl glucoside (degree of saccharide condensation: 1.28) as the dispersant, thereby providing distorted granular particles having extremely uneven surfaces. The average particle diameter and bulk density were 710 μm and 0.45 g/ml, respectively.

The measurement was conducted on the resultant polymer in the same manner as that of Example 4. The results are given in Table 1.

EXAMPLE 8

The same procedure as that of Example 4 was repeated except that tetradecyl glucoside (degree of saccharide condensation: 1.28) was used in addition to 0.9 g of the dodecyl glucoside (degree of saccharide condensation: 1.25) as the dispersant, thereby providing distorted granular particles having extremely uneven surfaces. The average particle diameter and bulk density were 800 μm and 0.47 g/ml, respectively.

The measurement was conducted on the resultant polymer in the same manner as that of Example 4. The results are given in Table 1.

EXAMPLE 9

The same procedure as that of Example 4 was repeated except that the dodecyl glucoside (degree of saccharide condensation: 1.25) was replaced with hexadecyl glucoside (degree of saccharide condensation: 2.5) as the dispersant, thereby providing distorted granular particles having extremely uneven surfaces. The average particle diameter and bulk density were 800 μm and 0.47 g/ml, respectively.

The measurement was conducted on the resultant polymer in the same manner as that of Example 4. The results are given in Table 1.

EXAMPLE 10

The same procedure as that of Example 4 was repeated except that the dodecyl glucoside (degree of saccharide condensation: 1.25) was replaced with 6-polyoxypropylene-dodecyl glucoside (degree of saccharide condensation: 1.3, 3 equivalent of polypropylene oxide adduct) as the dispersant, thereby providing distorted granular particles having extremely uneven surfaces. The average particle diameter and bulk density were 850 μm and 0.45 g/ml, respectively.

The measurement was conducted on the resultant polymer in the same manner as that of Example 4. The results are given in Table 1.

EXAMPLE 11

The same procedure as that of Example 4 was repeated except that the dodecyl glucoside (degree of saccharide condensation: 1.25) was replaced with dodecyl glucoside (degree of saccharide condensation: 1.6) as the dispersant, thereby providing distorted granular particles having extremely uneven surfaces. The average particle diameter and bulk density were 950 μm and 0.50 g/ml, respectively.

The measurement was conducted on the resultant polymer in the same manner as that of Example 4. The results are given in Table 1.

EXAMPLE 12

72.1 g of acrylic acid was diluted with 18.0 g of water and neutralized with 98.9 g of a 30 wt. % aqueous sodium hydroxide solution under cooling, and 10.7 g of a 2.8 wt. % aqueous potassium persulfate solution was added thereto to prepare a homogeneous solution.

Separately, a 500-ml flask equipped with a reflux condenser, a dropping funnel, a stirring rod and a nitrogen gas feed pipe was charged with 283 ml of cyclohexane, and 1.8 g of dodecyl glucoside (degree of saccharide condensation: 1.25) was added thereto. They were stirred (at 300 rpm) and dispersed in each other, and the flask was purged with nitrogen and heated to 75° C. The above-described aqueous acrylic acid (sodium salt) monomer solution was dropwise added thereto over a period of 30 min. After the completion of the addition, the polymerization was conducted under stirring at 75° C. for 1.5 h and then at 80° C. for 4 h. In the course of the polymerization, only water was continuously removed from the azeotropic reflux liquid comprising cyclohexane and water. When the water content of the acrylic acid (sodium salt) polymer gel had reached 30% by weight, 0.18 g of an epoxy bifunctional crosslinking agent (ethylene glycol diglycidyl ether) was added to conduct the reaction for 30 min. The resultant product was fractionated and dried under reduced pressure to provide 88.0 g of a partially crosslinked acrylic acid (sodium salt) polymer. The resultant polymer was in the form of distorted granular particles having an average diameter of 750 μm and a bulk density of 0.32 g/ml.

The measurement was conducted on the resultant polymer in the same manner as that of Example 4. The results are given in Table 1.

EXAMPLE 13

30.0 g of acrylic acid was diluted with 7.5 g of water and neutralized with 41.2 g of a 30 wt. % aqueous sodium hydroxide solution under cooling. 2.2 g of a 5.2 wt. % aqueous potassium persulfate solution, 0.030 g of an epoxy bifunctional crosslinking agent (ethylene glycol diglycidyl ether), 0.75 g of a sugar ester (trade name: Ryoto Sugar Ester S-507; a product of Mitsubishi-Kasei Foods Corporation) and 130 ml of cyclohexane were added thereto. The resulting mixture was stirred. After purging with nitrogen, an aqueous monomer solution (W/O emulsion) was obtained. Separately, a 500-ml flask equipped with a reflux condenser, a dropping funnel, a stirring rod and a nitrogen feed pipe was charged with 170 ml of cyclohexane, and 0.75 g of octyl glucoside (degree of saccharide condensation: 1.35) was added thereto. They were stirred (at 300 rpm) and dispersed in each other, and the flask was purged with nitrogen and heated to 75° C. The above-described aqueous monomer solution was dropwise added thereto over a period of 30 min. After the completion of the addition, the polymerization was conducted under stirring at 75° C. for 1.5 h and then at 80° C. for 4 h. After the completion of the polymerization, the resultant product was fractionated and dried under reduced pressure to provide 36.5 g of acrylic acid (sodium salt) polymer. The resultant polymer was in the form of distorted granular particles having an average diameter of 620 μm and a bulk density of 0.45 g/ml. The surfaces of the polymer particles had such a structure that the particles having irregular shapes and sizes of several to 20 μm were fused with each other and the unevenness of the surfaces was very large.

The measurement was conducted on the resultant polymer in the same manner as that of Example 4. The results are given in Table 1.

EXAMPLE 14

The same procedure as that of Example 4 was repeated except that the dodecyl glucoside (degree of saccharide condensation: 1.25) was replaced with 3-octadecanoyloxy-2-hydroxypropyl glucoside (degree of saccharide condensation: 1.27) as the dispersant, thereby providing distorted granular particles having extremely uneven surfaces. The average particle diameter and bulk density were 930 μm and 0.53 g/ml, respectively.

The measurement was conducted on the resultant polymer in the same manner as that of Example 4. The results are given in Table 1.

Comparative Example 1

An acrylic acid (sodium salt) polymer was produced in the same manner as that of Example 4, except that the dodecyl glucoside (degree of saccharide condensation: 1.25) was replaced with 0.9 g of ethylcellulose as the dispersant. The resultant polymer of acrylic acid (sodium salt) was in the form of spherical particles having a particle diameter of 330 μm and a bulk density of 0.94 g/ml.

The measurement was conducted on the resultant polymer in the same manner as that of Example 4. The results are given in Table 1.

Comparative Example 2

An acrylic acid (sodium salt) polymer was produced in the same manner as that of Example 4, except that the dodecyl glucoside (degree of saccharide condensation: 1.25) was replaced with 2.9 g of sorbitan monostearate (trade name: Rheodol SP-S10, a product of Kao Corporation) as the dispersant. The resultant polymer of acrylic acid (sodium salt) was in the form of a mixture of spherical particles having an average particle diameter of 50 μm and secondary particles comprising an aggregate of the spherical particles and having an average particle diameter of 590 μm, and had a bulk density of 0.65 g/ml. When the aggregate thus obtained was thrown into physiological saline, part of the secondary particles were easily converted into primary particles.

The measurement was conducted on the resultant polymer in the same manner as that of Example 4. The results are given in Table 1.

Comparative Example 3

An acrylic acid (sodium salt) polymer was produced in the same manner as that of Example 4, except that the dodecyl glucoside (degree of saccharide condensation: 1.25) was replaced with 1.8 g of polyoxyethylene sorbitan monostearate (trade name: Rheodeol TW-S106, a product of Kao Corporation) as the dispersant. The resultant polymer of acrylic acid (sodium salt) was in the form of comfit-shaped particles having a diameter of 3 to 30 mm and a bulk density of 0.68 g/ml.

The measurement was conducted on the resultant polymer in the same manner as that of Example 4. The results are given in Table 1.

Comparative Example 4

An acrylic acid (sodium salt) polymer was produced in the same manner as that of Example 4, except that the dodecyl glucoside (degree of saccharide condensation: 1.25) was replaced with 1.8 g of a sugar ester (trade name: Ryoto Sugar Ester S-1170; a product of Mitsubishi-Kasei Foods Corporation) as the dispersant. The resultant polymer of acrylic acid (sodium salt) was in the form of spherical particles having an average diameter of 13 μm and a bulk density of 0.59 g/ml.

The measurement was conducted on the resultant polymer in the same manner as that of Example 4. The results are given in Table 1.

Comparative Example 5

An acrylic acid (sodium salt) polymer was produced in the same manner as that of Example 12, except that the dodecyl glucoside (degree of saccharide condensation: 1.25) was replaced with 0.9 g of ethylcellulose as the dispersant. The resultant polymer of acrylic acid (sodium salt) was in the form of spherical particles having an average diameter of 350 μm and a bulk density of 0.93 g/ml.

The measurement was conducted on the resultant polymer in the same manner as that of Example 4. The results are given in Table 1.

TABLE 1

|  | Equil. swelling water absorption (g/g) | Water absorption (ml) | Passing rate (ml/min) |
| --- | --- | --- | --- |
| Ex. |  |  |  |
| 4 | 59 | 4.1 | 11.6 |
| 5 | 56 | 3.8 | 14.5 |
| 6 | 54 | 3.9 | 13.6 |
| 7 | 56 | 4.2 | 14.8 |
| 8 | 55 | 4.1 | 15.6 |
| 9 | 55 | 3.7 | 14.8 |
| 10 | 56 | 3.8 | 16.7 |
| 11 | 55 | 3.7 | 14.2 |
| 12 | 53 | 7.8 | 38.4 |
| 13 | 54 | 4.6 | 12.5 |
| 14 | 55 | 4.1 | 18.2 |
| Comp. Ex. |  |  |  |
| 1 | 53 | 2.7 | 2.3 |
| 2 | 55 | 3.5 | 1.5 |
| 3 | 53 | 3.6 | 5.4 |
| 4 | 51 | 2.5 | 1.3 |
| 5 | 53 | 2.8 | 5.4 |

EXAMPLE 15

2.0 g of acrylic acid was diluted with 25.5 g of water and partially neutralized with 140.0 g of a 30 wt. % aqueous sodium hydroxide solution under cooling, and 7.9 g of a 5.2 wt. % potassium persulfate solution was added thereto to prepare a homogeneous solution as the aqueous monomer/initiator solution. Separately, a 100-ml flask equipped with a reflux condenser, a dropping funnel, a stirring rod and a nitrogen gas feed pipe was charged with 400 ml of cyclohexane, and 2.55 g of N-(n-dodecyl)gluconamide was added thereto. They were stirred (at 350 rpm) and dispersed in each other, and the flask was purged with nitrogen and heated to 75° C. The above-described aqueous monomer/initiator solution was dropwise added thereto over a period of 1 h. After the completion of the addition of the acrylic acid monomer solution, the polymerization was conducted under stirring at 75° C. for 0.5 h and then at 80° C. for 4 h. After the completion of the polymerization, the granular gel thus formed was fractionated and dried under reduced pressure to provide 118.5 g of a polymer of acrylic acid (sodium salt). The resultant polymer was in the form of distorted granular particles having an average diameter of 530 μm and a bulk density of 0.36 g/ml. The surfaces of the polymer particles had such a structure that the particles having irregular shapes and sizes of several to 20 μm were fused with each other and the unevenness of the surfaces was very large.

EXAMPLE 16

100.6 g of acrylamide was dissolved in 212.2 g of water, and 7.9 g of a 2.8 wt. % aqueous 2,2'-azobis-(2-amidinopropane)dihydrochloride solution was added thereto to prepare a homogeneous solution as the aqueous monomer/initiator solution. Thereafter, the same procedure as that of Example 15 was repeated, except that n-hexane was used as the solvent instead of cyclohexane, thereby providing 98.5 g of an acrylamide polymer. The resultant polymer was in the form of distorted granular particles having an average diameter of 920 μm and a bulk density of 0.43 g/ml. The surfaces of the polymer particles had such a structure that the particles having irregular shapes and sizes of several to 20 μm were fused with each other and the unevenness of the surfaces was very large.

EXAMPLE 17

150.8 g of sodium acrylamidomethylpropanesulfonate was dissolved in 212.2 of water, and 7.9 g of a 2.8 wt. % aqueous 2,2'-azobis(2-amidinopropane)dihydrochloride solution was added thereto to prepare a homogeneous solution as the aqueous monomer/initiator solution. Thereafter, the same procedure as that of Example 15 was repeated, thereby providing 133.7 g of a sodium acrylamidomethylpropanesulfonate polymer. The resultant polymer was in the form of distorted granular particles having an average diameter of 1000 μm and a bulk density of 0.52 g/ml. The surfaces of the polymer particles had such a structure that the particles having irregular shapes and sizes of several to 20 μm were fused with each other and the unevenness of the surfaces was very large.

EXAMPLE 18

102.0 g of acrylic acid was diluted with 25.5 g of water and partially neutralized with 140.0 g of a 30 wt. % aqueous sodium hydroxide solution under cooling, and 7.9 g of a 5.2 wt. % aqueous potassium persulfate solution and 0.082 g of an epoxy bifunctional cross-linking agent (ethylene glycol diglycidyl ether) were added thereto to prepare a homogeneous solution as the aqueous monomer/initiator solution. Separately, a 1000-ml flask equipped with a reflux condenser, a dropping funnel, a stirring rod and a nitrogen gas feed pipe was charged with 400 ml of cyclohexane, and 2.55 g of N-(n-dodecyl gluconamide was added thereto. They were stirred (at 350 rpm) to obtain a dispersion, and the flask was purged with nitrogen and heated to 75° C. The above-described aqueous monomer/initiator solution was dropwise added thereto over a period of 1 h. After the completion of the addition of the acrylic acid monomer solution, the polymerization was conducted under stirring at 75° C. for 0.5 h and then at 80° C. for 4 h. After the completion of the polymerization, the resultant granular gel was fractionated and dried under reduced pressure to provide 117.2 g of a polymer of acrylic acid (sodium salt). The resultant polymer was in the form of distorted granular particles having an average diameter of 570 μm and a bulk density of 0.38 g/ml. The surfaces of the polymer particles had such a structure that the particles having irregular shapes and sizes of several to 20 μm were fused with each other and the unevenness of the surfaces was very large. The measurement was conducted on the resultant polymer particles in the same manner as that of Example 4. The results are given in Table 2.

EXAMPLE 19

51.1 g of acrylic acid was diluted with 22.6 g of water and neutralized with 75.0 g of a 30 wt. % aqueous sodium hydroxide solution under cooling. Thereafter, 143.3 of a 40 wt. % aqueous sodium acrylamidomethylpropanesulfonate solution was added thereto, and then 7.9 g of a 5.2 wt. % aqueous potassium persulfate solution and 0.082 g of epoxy bifunctional cross linking agent (ethylene glycol diglycidyl ether) were added thereto to prepare a homogeneous solution as the aqueous monomer/initiator solution. Thereafter, the same procedure as that of Example 18 was repeated, thereby providing 131.5 g of a sodium acrylate/sodium acrylamidomethylpropanesulfonate copolymer. The resultant polymer was in the form of distorted granular particles having an average diameter of 580 μm and a bulk density of 0.44 g/ml. The measurement was conducted on the resultant polymer particles in the same manner as that of Example 4. The results are given in Table 2.

EXAMPLE 20

The same procedure as that of Example 18 was repeated except that the N-(n-dodecyl)gluconamide was replaced with N-(n-decyl)gluconamide as the dispersant, thereby providing 116.7 g of distorted granular particles having extremely uneven surfaces. The average particle diameter and bulk density were 670 μm and 0.47 g/ml, respectively. The measurement was conducted on the resultant polymer particles in the same manner as that of Example 4. The results are given in Table 2.

EXAMPLE 21

The same procedure as that of Example 18 was repeated except that the N-(n-dodecyl)gluconamide was replaced with N-(n-tetradecyl)gluconamide as the dispersant, thereby providing 117.5 g of distorted granular particles having extremely uneven surfaces. The average particle diameter and bulk density were 530 μm and 0.46 g/ml, respectively. The measurement was conducted on the resultant polymer particles in the same manner as that of Example 4. The results are given in Table 2.

EXAMPLE 22

The same procedure as that of Example 18 was repeated except that N-(n-decyl)gluconamide was used in addition to 1.25 g of the N-(dodecyl)gluconamide, thereby providing 118.1 g of distorted granular particles having extremely uneven surfaces. The average particle diameter and bulk density were 600 μm and 0.40 g/ml, respectively. The measurement was conducted on the resultant polymer particles in the same manner as that of Example 4. The results are given in Table 2.

EXAMPLE 23

The same procedure as that of Example 18 was repeated except that the N-(n-dodecyl)gluconamide was replaced with N-(n-hexadecyl)gluconamide as the dispersant, thereby providing 117.5 g of distorted granular particles having extremely uneven surfaces. The average particle diameter and bulk density were 630 μm and 0.52 g/ml, respectively. The measurement was conducted on the resultant polymer particles in the same manner as that of Example 4. The results are given in Table 2.

EXAMPLE 24

The same procedure as that of Example 18 was repeated except that the N-(n-dodecyl)gluconamide was replaced with N-(n-octadecyl)gluconamide as the dispersant, thereby providing 117.7 g of distorted granular particles having extremely uneven surfaces. The average particle diameter and bulk density were 720 μm and 0.55 g/ml, respectively. The measurement was conducted on the resultant polymer particles in the same manner as that of Example 4. The results are given in Table 2.

EXAMPLE 25

The same procedure as that of Example 18 was repeated except that 0.50 g of a sugar ester (Ryoto Sugar Ester S-570; a product of Mitsubishi-Kasei Foods Corporation) was used in addition to 2.55 g of N-(n-dodecyl)gluconamide as the dispersant, thereby providing 118.8 g of distorted granular particles having extremely uneven surfaces. The average particle diameter and bulk density were 610 μm and 0.53 g/ml, respectively. The measurement was conducted on the resultant polymer particles in the same manner as that of Example 4. The results are given in Table 2.

EXAMPLE 26

102.0 g of acrylic acid was diluted with 25.5 g of water and neutralized with 140.0 g of a 30 wt. % aqueous sodium hydroxide solution under cooling, and 7.9 g of a 5.2 wt. % aqueous potassium persulfate solution was added thereto to prepare a homogeneous solution as the aqueous monomer/initiator solution. Separately, a 1000-ml flask equipped with a reflux condenser, a dropping funnel, a stirring rod and a nitrogen gas feed pipe was charged with 400 ml of cyclohexane, and 2.55 g of N-(n-dodecyl)gluconamide was added thereto. The resultant mixture was stirred (at 350 rpm) to obtain a dispersion, and the flask was purged with nitrogen and heated to 75° C. The above-described aqueous monomer/initiator solution was dropwise added thereto over a period of 30 min. After the completion of the addition, the polymerization was conducted under stirring at 75° C. for 1.5 h and then at 80° C. for 4 h. In the course of the polymerization, only water was continuously removed from the azeotropic reflux liquid comprising cyclohexane and water. When the water content of the acrylic acid (sodium salt) polymer particles had reached 30% by weight, 0.25 g of an epoxy bifunctional crosslinking agent (ethylene glycol diglycidyl ether) was added to conduct the reaction for 30 min. The resultant partially crosslinked acrylic acid (sodium salt) polymer was taken out and dried. The granular particles thus obtained were fractionated and dried under reduced pressure to obtain 119.3 g of an acrylic acid (sodium salt) polymer. The resultant polymer was in the form of distorted granular particles having an average diameter of 510 μm and a bulk density of 0.35 g/ml. The measurement was conducted on the resultant polymer particles in the same manner as that of Example 4. The results are given in Table 2.

Comparative Example 6

The same procedure as that of Example 18 was repeated except that the N-(n-dodecyl)gluconamide was replaced with 0.9 g of ethylcellulose as the dispersant, thereby providing 116.9 g of a polymer. This acrylic acid (sodium salt) polymer was in the form of spherical particles having an average particle diameter and a bulk density of 330 μm and 0.94 g/ml, respectively. The measurement was conducted on the resultant polymer particles in the same manner as that of Example 4. The results are given in Table 2.

Comparative Example 7

117.9 g of a polymer was produced in the same manner as that of Example 18, except that the N-(n-dodecyl)gluconamide was replaced with 2.9 g of sorbitan monostearate (trade name: Rheodol SP-S10) as the dispersant. The resultant polymer of acrylic acid (sodium salt) was in the form of a mixture of spherical particles having an average particle diameter of 50 μm and secondary particles comprising an aggregate of the spherical particles and having an average particle diameter of 590 μm, and had a bulk density of 0.65 g/ml. When the aggregate thus obtained was thrown into physiological saline, part of the secondary particles were easily converted into primary particles. The measurement was conducted on the resultant polymer particles in the same manner as that of Example 4. The results are given in Table 2.

Comparative Example 8

117.9 g of a polymer was produced in the same manner as that of Example 18, except that the N-(n-dodecyl)gluconamide was replaced with 1.8 g of polyoxyethylene sorbitan monostearate (trade name: Rheodol TW-S106, a product of Kao Corporation) as the dispersant. The resultant polymer of acrylic acid (sodium salt) was in the form of comfit-shaped particles having a diameter of 3 to 30 mm and a bulk density of 0.68 g/ml. The measurement was conducted on the resultant polymer particles in the same manner as that of Example 4. The results are given in Table 2.

Comparative Example 9

118.6 g of a polymer was produced in the same manner as that of Example 18, except that the N-(n-dodecyl)gluconamide was replaced with 1.8g of a sugar ester (trade name: Ryoto Sugar Ester S-1170; a product of Mitsubishi-Kasei Foods Corporation) as the dispersant. The resultant polymer of acrylic acid (sodium salt) was in the form of spherical particles having an average diameter of 13 μm and a bulk density of 0.59 g/ml. the measurement was conducted on the resultant polymer particles in the same manner as that of Example 4. The results are given in Table 2.

Comparative Example 10

118.3 g of a polymer was produced in the same manner as that of Example 26, except that the N-(n-dodecyl)gluconamide was replaced with 0.9 g of ethylcellulose as the dispersant. The resultant polymer of acrylic acid (sodium salt) was in the form of spherical particles having an average diameter of 350 μm and a bulk density of 0.93 g/ml. The measurement was conducted on the resultant polymer particles in the same manner as that of Example 4. The results are given in Table 2.

TABLE 2

| | Equil. swelling water absorption (g/g) | Water absorption (ml) | Passing rate (ml/min) |
|---|---|---|---|
| Ex. | | | |
| 18 | 57 | 4.4 | 12.2 |
| 19 | 57 | 3.3 | 13.2 |
| 20 | 58 | 3.7 | 12.8 |
| 21 | 59 | 3.0 | 15.1 |
| 22 | 59 | 4.0 | 13.7 |
| 23 | 58 | 3.3 | 13.3 |
| 24 | 58 | 3.5 | 18.9 |
| 25 | 59 | 3.2 | 12.6 |
| 26 | 52 | 7.5 | 40.2 |
| Comp. Ex. | | | |
| 6 | 53 | 2.7 | 2.3 |
| 7 | 55 | 3.5 | 1.5 |
| 8 | 53 | 3.6 | 5.4 |
| 9 | 51 | 2.5 | 1.3 |
| 10 | 53 | 2.8 | 5.4 |

What is claimed is:

1. A process for producing polymer particles with a nonspherical shape by polymerizing a water-soluble polymerizable monomer in a system comprising (1) a hydrophobic organic solvent inert to the polymerization, (2) an aqueous solution of the water-soluble polymerizable monomer, and (3) a dispersant comprising:

(a) a glycoside compound wherein the hydrogen atom of the hemiacetal hydroxy group in the compound has been replaced with a hydrophobic group, and having the following formula (1)

$$R^1(OR^2)_xG_y \qquad (1)$$

wherein $R^1$ represents a linear or branched alkyl, alkenyl group, or an alkylphenyl group having 6 to 22 carbon atoms, or a hydroxyacyloxyalkyl group having at least 9 carbon atoms, $R^2$ represents an alkylene group having 2 to 4 carbon atoms, G represents a reducing sugar residue having 5 or 6 carbon atoms, x represents a number of 0 to 10 on average and y represents a number of 1 to 10 on average, with the proviso that when x is 2 or above, then each $R^2$ may be the same or different from each other, and the hydrogen atom of a hydroxyl group in G may be substituted by a methyl group, an ethyl group, or a group having 12 or fewer carbon atoms and at least one hydrophilic group such as an ether oxygen, ester group, amido group, ionic group, hydroxyl group or ammonium group; or (b) a gluconamide compound having the following formula (11):

wherein R and $R_1$ each represent a hydrogen atom a linear or branched alkyl or alkenyl group having 5 to 25 carbon atoms, a phenyl group or an alkylaryl group having 7 to 25 carbon atoms, with the proviso that not both of R and $R_1$ are hydrogen atoms at the same time, and R and $R_1$ may contain a functional group such as a hydroxyl, ether, oxyalklene or acetyl group.

2. A process for producing polymer particles with a nonspherical shape by polymerizing a water-soluble polymerizable monomer in a system comprising (1) a hydrophobic organic solvent inert to the polymerizable monomer, (2) and aqueous solution of the water-soluble polymerizable monomer, and (3) a dispersant comprising:

(a) a gylcoside compound having the following formula (2):

$$R^3 G'_{y'} \quad (2)$$

wherein $R^3$ represents a linear or branched alkyl, alkenyl group, or an alkylphenyl group having 6 to 22 carbon atoms, or a hydroxyacyloxyalkyl group having 9 to 25 carbons atoms, $G'$ represents a reducing sugar residue having 5 or 6 carbon atoms and $y'$ represents a number of 1 to 6 on average.

3. A process for producing polymer particles with a nonspherical shape by polymerizing a water-soluble polymerizable monomer in a system comprising (1) a hydrophobic to organic solvent inert to the polymerization, (2) an aqueous solution of the water-soluble polymerizable monomer, and (3) a dispersant comprising:

(a) glycoside compound having the following formula (10):

$$R^4 G''_{y''} \quad (10)$$

wherein $R^4$ represents a linear or branched alkyl, alkenyl group, or an alkylphenyl group having 6 to 22 carbon atoms, or a hydroxyacyloxyalkyl group having 9 to 25 carbon atoms, $G''$ represents a reducing sugar residue having 5 or 6 carbon atoms wherein the hydrogen atom of the hydroxyl group is substituted for a polyoxyethylene, polyoxypropylene or polyglyceryl group and $y''$ represents a number of 1 to 6 on average.

4. A process for producing polymer particles with a nonspherical shape according to any of claims 1, 2, or 3, wherein said water-soluble polymerizable monomer is an olefinically unsaturated carboxylic acid or an alkali salt thereof.

5. A process for producing polymer particles with a nonspherical shape according to claim 4, wherein said water-soluble polymerizable monomer is acrylic acid, methacrylic acid, maleic acid, fumaric acid or an alkali salt thereof.

* * * * *